United States Patent [19]

Lewis et al.

[11] Patent Number: 5,045,328

[45] Date of Patent: Sep. 3, 1991

[54] TREATING PARBOILED GRAINS AND PRODUCTS

[76] Inventors: Victor M. Lewis; David A. Lewis, both of 19A Boundary Street, Rushcutters Bay, New South Wales, 2011, Australia

[21] Appl. No.: 614,671

[22] Filed: Nov. 15, 1990

Related U.S. Application Data

[63] Continuation of Ser. No. 356,594, May 23, 1989, abandoned, which is a continuation of Ser. No. 5,156 filed as PCT AU 86/00089 on Apr. 7, 1986, published as WO86/05953 on Oct. 23, 1986, abandoned:

[30] Foreign Application Priority Data

Apr. 15, 1985 [AU] Australia .......................... PH00149

[51] Int. Cl.[5] ...................... A23L 1/10; A23L 1/105; A23L 1/182

[52] U.S. Cl. ...................................... 426/28; 426/52; 426/63; 426/64; 426/618; 426/620

[58] Field of Search ...................... 426/28, 52, 63, 64, 426/618, 620

[56] References Cited

U.S. PATENT DOCUMENTS

| | | |
|---|---|---|
| 2,930,697 | 3/1960 | Miller . |
| 3,851,085 | 11/1974 | Rodgers et al. . |
| 3,870,804 | 3/1975 | Tolson, Sr. et al. . |
| 3,996,384 | 12/1976 | Reesman et al. . |
| 4,254,150 | 3/1981 | Fritze et al. . |
| 4,361,593 | 11/1982 | Brooks et al. . |

FOREIGN PATENT DOCUMENTS

| | | | |
|---|---|---|---|
| 167768 | 4/1954 | Australia . | |
| 495512 | 1/1977 | Australia | 426/618 |
| 4063078 | 5/1980 | Australia . | |
| 9002582 | 5/1983 | Australia . | |
| 1642553 | 5/1971 | Fed. Rep. of Germany . | |
| 55-3769 | 1/1980 | Japan . | |
| 1128286 | 9/1968 | United Kingdom . | |
| 1232275 | 5/1971 | United Kingdom . | |
| 2116415 | 9/1983 | United Kingdom . | |

OTHER PUBLICATIONS

Marc et al., "A Kinetic Model of Starch Hydrolysis by-and-Amylase During Mashing", *Biotechnology and Bioengineering,* vol. XXV, pp. 481–496, (1983).

Hausser et al., "An Immobilized Two-Enzyme System (Fungal-Amylase/Glucoamylase) and Its Use in the Continuous Production of High Conversion Maltose-Containing Corn Syrups", *Biotechnology and Bioengineering,* vol. XXV, pp. 525–539 (1983) (Hausser et al.).

*Primary Examiner*—Joseph Golian

*Attorney, Agent, or Firm*—Scully, Scott, Murphy & Presser

[57] ABSTRACT

Process of producing a grain product which comprises subjecting parboiled grain to compression by rolling the grains being maintained at temperatures prior to and during compression below gelatinization temperature. In certain cases the compression step is omitted and an improved product can be obtained by subjecting the grains to treatment with a solution containing an enzyme or enzymes, the quantity of the solution used is such that it is totally absorbed by the grain. In other cases the two aforementioned processes are combined in which case the grain is treated with a solution containing a measured quantity of a solution containing an enzyme or enzymes the quantity of the solution is such that it is totally absorbed by the grains, thereafter the grains are subject to compression by rolling. The invention also relates to a grain product produced by said process.

14 Claims, No Drawings

TREATING PARBOILED GRAINS AND PRODUCTS

This is a continuation of application Ser. No. 356,594, filed on May 23, 1989, and now abandoned, which in turn is a continuation of application Ser. No. 005,156, filed as PCT AU86/00089 on Apr. 7, 1986, published as WO86/05953, on Oct. 23, 1986, now abandoned.

Rice is prepared for table consumption in various ways, the most common of which is by cooking whole from the dry state using various cooking procedures. Rice is also precooked then ground to a flour for use in infants and invalids foods. Rice is also toasted to develop an expanded light texture and a highly browned color. Such rice is used as a breakfast cereal and also finds application in certain confectionery products such as "Granola" bars, "Muesli" bars and in other product applications where a light crispy texture and low bulk density is desired. Toasted expanded ready-to-eat rice is hereafter referred to as "crisped rice".

Rice for cooking (hereafter referred to as cooking rice) often suffers from a tendency for the cooked rice to finish up sticky, gluggy and cohesive, both when freshly cooked and on cooling. On cooling, cooked rice often becomes excessively firm. By contrast, most consumers prefer cooked rice to be of a fluffy texture with the grains separate and non-sticky, yet still reasonably firm. The present invention from one aspect relates to rice which (a) is significantly less sticky, or not sticky at all when cooked, or when it has cooled down after cooking;

(b) when cooked and cooled is not excessively firm.

From this aspect the invention is applicable to regular rice, but is particularly applicable to quick-cooking rice. It is also applicable to other grains, and particulate grain products.

Crisped rice often suffers from being too heavy (i.e. too high a bulk density), and has a tendency of having a high proportion of broken grains. Rice of this type is costly to produce and it is difficult for the processor to maintain manufacturing specifications, particularly those relating to bulk density and=holeness. It also tends to have a bubbly uneven surface, such that when packaged, shipped and otherwise handled the fine surface bubbles of individual grains tend to fracture producing a dusty sediment and unattractive appearance.

The present invention from another aspect relates to the production of crisped rice in an economical way, with the ability to achieve very low bulk densities in the finished product if desired, and with the ability also to be able to produce a product of particular bulk density and degree of grain wholeness by easy adjustment and control of the process whereby the crisped rice is produced. In addition the surface of crisped rice produced by this invention has a smoother surface which fractures less. The invention is also applicable to certain other crisped grain products.

Other important advantages will be apparent from the description of the process and the products.

The present invention utilizes two effects, both of which contribute both separately and jointly in a novel way to the described results. The first of these is called "cold-rolling" and the second is called "low moisture enzyme treatment" hereafter called LMET.

The term "cold-rolling" is used here to describe the subjection of grains or particles thereof to compression, for example by means of passing the grains between rotating rolls, smooth or slightly grooved rotating at the same or almost the same speed, such that during the rolling process the temperature of the grains is at ambient temperature or at a temperature below that at which gelatinization will occur or at which de-retrogradation of gelatinized starch already in the grains will occur. Thus cold-rolling of grains as above described is in marked contrast to the usual method of rolling grains and grain products to induce compression effects whereby the products are rolled or compressed at elevated temperatures, of the order of a low of 65° C.–70° C. but more usually at 90° C.–100° C. for example immediately or soon after steaming, under which conditions any gelatinized starch will not have had an opportunity to retrograde; if the product was already in a gelatinized condition before steaming, steaming would have caused de-retrogradation of the gelatinized starch present prior to said steaming.

The precise mechanism whereby cold-rolling has these effects on rice for cooking is not known for certain. However, it is believed that cold-rolling has an effect of breaking down to some extent the crystalline organized or basic gel structure of the starch matrix in the grain in such a way that the grain, when cooked in water, allows, on the one hand, more rapid entry of water into the grain and on the other hand, acts to prevent or substantially reduce de-retrogradation of the gelatinized starch during the final cooking process in the home. As a consequence of this, the rice is more tender and less firm and rubbery when cooked as well as when cooled down after cooking. By contrast, when parboiled grains have been steamed, then hot rolled promptly thereafter, most of the starch, being in a de-retrograded form as it comes from the steamer, is merely deformed by the hot rolling. On cooling, the starch again retrogrades to form a highly organized or crystalline matrix. When cooked, this hot rolled rice has a distinctly more rubbery or bouncy mouth-feel and is less acceptable than the above described cold-rolled product.

The effect of cold-rolling on the subsequent expansion of crisped grains is also most surprising. The mechanism of the effect is not known for certain. It is considered to be related to a physical disruption of the organized state of the gelatinized starch matrix with the consequence that the matrix is less able to restrain the expansion of the grain under the influence of high toasting temperatures and the expanding gases and moisture vapor within the grain. By contrast, hot rolling of grain merely deforms the shape of the grain, making it thinner and hence allowing only more rapid heating during the actual toasting operation. When the grain has been hot rolled, the required pre-heating step changes the starch to its non-retrograded condition. Its subsequent cooing and tempering results in retrogradation of the gelatinized starch into a highly organized matrix which is considered to have a restraining action on expansion during the final toasting operation. The consequence of this is lesser expansion and therefore higher bulk density, and a tendency to produce harder, less acceptable crisped grains.

It is a further characteristic of rice which has been cold-rolled as described herein that gelatinized starch present in a cold-rolled product displays a unique and novel characteristic when examined in a differential scanning calorimeter (D.S.C.). It is common practice for products to be examined or "scanned" in a D.S.C. and for the same sample to be "re-scanned" at a later stage, commonly two or four days later. In contrast to all other rice samples examined, the four-day re-scan of cold-rolled rice does not show the typical strong endotherm considered to be related to de-retrogradation of gelatinized starch from the initial scan in the D.S.C. It is unique and novel for starch-containing parboiled or pre-cooked products, when examined in a D.S.C. to produce an initial scan and a re-scan (typically 2–4 days later), to show re-scan de-retrogradation endotherms (RDE's) which are either similar to or less than the initial de-retrogradation endotherms (IDE's). In our work, most of the RDE's are substantially less than and often less than 50% of the IDE's. Products having this characteristic when examined in a D.S.C. are quite unique.

The term LMET is used here to describe the treatment of grains or grain particles with enzymes, especially amylases but also, to a lesser extent, proteases, whereby the enzymes, in aqueous solution or dispersion, with or without other substances, are absorbed by the grain in totality such that the moisture content of the product, after having totally absorbed the enzyme-bearing solution is at a very low level, for example 16%–30% approximately, more usually 19%–26%.

Such low levels of moisture as specified above, in relation to treatment of foods with enzymes is quite unusual since it is usual when using enzymes on starch substrates to treat the gelatinized starch in water with amylases at a starch concentration of 10%–15% or occasionally up to 20%. With particulate substances steeped in aqueous enzyme solutions it may be possible to work at a substrate concentration as low as 44% or 45% (calculated on the basis of the ratio - substrate:substrate + water).

LMET has many advantages, namely:

1) large volumes of liquids are not required, nor is it necessary to carry out steeping and draining operations all of which are messy, requiring the use of tanks and other ancillary equipment. High moisture treatments are subject to wastage and lack of precise control when used in commercial operations;
2) the grain product, once moistened, rapidly absorbs the small amount of enzyme solution and quickly becomes free flowing and easy to handle;
3) because of the low moisture content of the product final drying operations are quick and economical;
4) because the enzyme solution is fully absorbed by the product, the concentrations of enzyme, moisture and other substances are known precisely;
5) this allows for simple ways of varying the nature of the treatment and hence the degree of effect achieved.

The desirable effects of LMET on both the cooking quality of rice and other products described as well as on the expansion of crisped grains, is quite unexpected. Indeed, it is surprising that under the relatively low moisture conditions described, the enzymes have any effect on the products, since we have not found descriptions of the use and effectiveness of enzymes under such low moisture conditions. The precise mechanism of these desirable effects is not known for certain. However, it is believed that the enzyme treatment under the conditions described has a limited but effective influence on the gelatinized matrix or crystal structure of the grain. In the case of grains to be crisped, the enzyme is considered to have a relaxing effect on the otherwise confining influence of the gelatinized matrix so that when the treated material is toasted at the high temperature used, the moisture vapor and other gases can act to expand the grain structure to a greater extent than is possible when the matrix has not been subjected to the influence of LMET. This relaxing influence may be of a similar nature to the apparent physical disruption of the matrix postulated for the cold-rolling process, but we are inclined to think that it is a distinct mechanism, since our observations clearly show the effects of cold-rolling and LMET to be synergistic and cumulative.

With respect to the effect of LMET on products for cooking, such as quick-cooking parboiled rice, we consider the relaxing effect of the enzymes on the gelatinized starch chains in the integral grain tissue results in the easier access of cooking water to the dry interior part of the tissue or food material It is believed that the enzyme under the conditions of LMET is probably effecting a minimal and controlled rupturing of the starch molecules to produce intermolecular channels whereby the moisture may more readily gain access into the interior parts. At the same time, the reduced cohesiveness of grains which have been subjected to LMET probably resides in the solubilization of the loose surface starch or free starch molecule chains at the surface of the grains or other products. It is believed that the stickiness, glugginess or cohesiveness of many cooked starchy particulate foods is caused by loose starch on the surface and by free starch molecule chains at the surface of the food particle which are not bound into the well-integrated matrix of the body of the food particle. By solubilizing this surface starch or loose superficial starch molecule chain, this cohesive tendency is substantially reduced or eliminated.

It is considered that the removal of free surface starch and stickiness as described is responsible for the less starchy cooked flavor of other foods which have been subjected to LMET (as compared to regular products). In addition, removal of this slickiness allows for ready cooking in much smaller volumes of water than is normal, or by total absorption, since the cooking water does not contain dispersed starch to the extent that is the case when regular products are cooked in a limited amount of water or by total absorption.

The invention according to one form resides in a process of producing a grain product which comprises subjecting parboiled grains to compression by rolling said grains prior to and during said compression being maintained at temperatures below gelatinization temperature.

The invention according to a further form resides in a process of producing a grain product which comprises subjecting a parboiled grain to treatment with a measured quantity of a solution containing at least an enzyme or enzymes, the quantity of the solution being such that it is totally absorbed by the grain, holding the grain for a period of time to permit penetration of the solution throughout the grain without a substantial loss of moisture from the grains and for the enzyme or enzymes to act on said grains and thereafter subjecting the grains to compression by rolling.

Preferably the grain is maintained at a temperature below gelatinization and the solution is absorbed by the grain in 3 to 20 minutes.

The invention according to a still further form relates to a process of producing a grain product which comprises subjecting parboiled grain to treatment with a measured quantity of solution containing at least an enzyme or enzymes, the quantity of the solution being such that it is totally absorbed by the grain and subsequently removing the surface moisture from the grain.

It is within the scope of the invention that other additives such as sodium chloride, sugars, flavorings, coloring substances, seasonings, preservatives, nutritional supplements and anti-oxidants may be incorporated in the grain along with the added moisture and enzymes.

The invention also relates to grain products including crisped grain products having improved characteristics produced from grains processed in accordance with the invention. One particular characteristic of grain products processed according to the invention is that the product when subjected to examination on a differential scanning calorimeter shows an endotherm on rescanning which is equal to or less than the endotherm on the initial scan.

The methods of application of cold-rolling and of low-moisture enzyme treatment are now described in the following detailed examples. It will be understood however that the specific details included in the given examples should not be regarded as limiting. By controlled variation of the operating parameters, which are simple to achieve because of the nature of the component steps involved, it is possible to produce finished products having particular desired characteristics, which may be different from those in the particular examples given hereunder.

EXAMPLE 1

Long-grain American parboiled rice typically at a moisture content of 12.0% was subjected to various treatments as follows.

Treatment A, the rice was gently mixed (in a slow speed tumbling-action device) with a measured quantity of water containing an amylase, BAN-240L (manufactured by Novo Industri, Denmark) at the rate of 1 g Enzyme preparation per kilo of dry rice. The water was fully absorbed in 5 minutes after which the moisture content of the rice was 24%. The dampened rice was held for 15 hours at ambient temperature such that no moisture loss occurred to allow uniform penetration of the moisture throughout the rice. The rice was then subjected to compression by rolling at ambient temperature ("cold-rolled") between smooth rolls set so that the gap between them was 0.32 mm. The rice was then dried back to 12% moisture.

Treatment B, the rice was treated as in Treatment A except that no enzyme was added to the water used to increase the moisture content to 24%. It was observed that the rice grains during tempering at 24% moisture were more cohesive than in the case of Treatment A but not excessively so.

Treatment C, the rice was gently mixed with water as in example A, at the rate of 50 ml per kg of rice for 5 minutes, then steamed in live dry steam at atmospheric pressure (100° C.) for 5 minutes. The steaming hot rice was rolled between smooth rolls set so that the gap between them was 0.32 mm. The rolled still-warm rice was gently mixed with the amylase preparation BAN 240L at the rate of 1 g per kilo of dry rice, the preparation being first dispersed in warm water at a dilution of 1 g per 100 g water. The enzyme solution was readily absorbed by the previously hot-rolled rice. The rice was dried back to 12% moisture after having been held warm for 15 minutes subsequent to addition of the enzyme solution.

Treatment D, the rice was treated as in treatment A, except that after the solution of amylase in water was fully absorbed (after 5 minutes mixing) the rice was heated to 50° C. and held at this temperature for 50 minutes. While still at this temperature it was rolled as in treatment A. Since this temperature is below the gelatinization temperature for rice, the rice is regarded as having been "cold rolled" as defined earlier.

These various rices were compared for cooking and eating characteristics with the untreated long-grain parboiled rice (control):

| TREATMENT | COOKED (lid on) | TASTING COMMENTS HOT | TASTING COMMENTS COLD | ORDER OF RATING FOR ALL CHARACTERS (Best = 1) |
|---|---|---|---|---|
| Control | 100 g rice in 250 ml water. Simmer 20 mins, let stand 5 mins. | Firm-cooked slightly sticky or cohesive on standing, starchy flavour. | Rice grains excessively firm, slightly sticky or cohesive. | 3 |
| A | 100 g rice in 200 ml water. Simmer 8-10 mins. | Rice well cooked in 8 mins, grains extremely separate & tender. Flavour excellent - less starchy than control. | Rice grains tender & acceptable though firmer than when hot; grains extremely separate. Superior to control in every respect. | 1 |
| B | 100 g rice in 200 ml water. Simmer 8-10 mins. | Rice well cooked in 8 mins, grains extremely separate & tender. Flavour excellent - less starchy than control. | Rice grains tender & acceptable though firmer than when hot; grains extremely separate. Superior to control in every respect. | 1 |
| C | 100 g rice in 200 ml water. Simmer 10 mins. | Rice well cooked in 10 mins, grains extremely separate; tender. Flavour excellent - less starchy than control. Grains more tender than control but less tender than treatment A. | Rice grains reasonably tender. Grains extremely separate and superior to control in every respect. | 2 |
| D | 100 g rice in 200 ml water. Simmer 10 mins. | Rice reasonably cooked in 10 mins, reasonably separate and tender. | Rice grains reasonably tender & separate. | 2 |

Cold-rolling with or without low moisture enzyme treatment will produce very good rice and a combination of cold-rolling and low moisture enzyme treatment results in the best rice, judged on shortness of cooking time, tenderness and separateness of grains (when hot, and likewise when cold) and flavor. Hot-rolling in conjunction with low moisture enzyme treatment produced very good rice. All these treatments for rice were judged to produce products significantly superior to the control.

Rice treated according to A, B, C and D were also compared with the control in relation to the pattern shown when examined in the D.S.C. Samples of the various treatments and the control were ground to a coarse flour, sieved to obtain uniform particle size then mixed with an equal weight of water before weighing and sealing into the D.S.C. sample cans. Results below list the measure of the endotherm displayed in the initial scan and the 4-day re-scan. Results for a commercial quick cooking rice are also included.

| | Measure of Endotherm (initial scan) | Measure of Endotherm (4 day re-scan) | Comments |
|---|---|---|---|
| Control | 0.17 J./g. | 1.87 J./g. | Strong typical retrogradation endotherm on 4 day re-scan |
| B No enzyme treatment - cold rolled | 1.03 J./g. | 0.66 J./g. | Significantly reduced retrogradation endotherm on 4 day re-scan |
| A Enzyme treated - cold rolled | 0.65 J./g. | 0.35 J./g. | Significantly reduced retrogradation endotherm on 4 day re-scan |
| C Steamed - hot rolled - enzyme treated | 0.56 J./g. | 2.15 J./g. | Strong typical retrogradation endotherm on 4 day re-scan |
| D Enzyme treated cold rolled at 50° C. | 0.28 J./g. | 0.24 J./g. | Reduced retrogradation endotherm on 4 day re-scan |
| "Minute Rice" fully pre-cooked instant rice | insignificantly small figure | 2.18 J./g. | Strong typical retrogradation endotherm on 4 day re-scan |

It is clear from the above results that pre-tempering and cold-rolling induces a change or changes in parboiled rice which are unique in relation to regular parboiled rice, to quick-cooking parboiled rice processed by hot-rolling and to fully pre-cooked instant rice. These changes are very clearly shown in terms of a very low retrogradation endotherm on a 2-day or 4-day D.S.C. re-scan which is either slightly or substantially less than the initial scan endotherm and commonly less than half of the initial. The changes induced by cold-rolling also contribute to a high degree of separateness and tenderness of the rice when cooked and observed hot and on cooling, as well as to other effects described later.

It has been found that long-grain parboiled brown rice when treated by methods resembling treatments A, B, C and D also gives similar results and improvements though the gap through which the rice is rolled needs to be slightly wider.

While most rice is consumed in a cooked whole-grain form, there is also an important demand and need for pre-cooked rice flour or flakes for use in infant foods, gruels and other special diet foods. Existing methods for the manufacture of these products require the fully precooking of rice to a high moisture content, then drying of the soft rice grains or of a paste made therefrom on roller dryers. The product is accordingly very expensive to produce because of the high energy requirement and the low-capacity expensive drying equipment. We have found that by use of low-moisture enzyme treatment it is practicable and economical to produce a precooked rice flour very economically, which flour is suitable for use in infant foods and the like such that addition of boiling water to the flour results in a digestible, non-starchy-tasting base for such diet foods.

For the production of crisped rice by known methods, rice in dry precooked form, after having been subjected to involved and lengthy pre-preparation and flavoring steps and operations, is finally toasted in very hot rapidly moving air, typically at a temperature of 220° C.-270° C. often in a tumbling device, under which conditions the rice rapidly expands, sets in this expanded condition, and becomes lightly toasted in color and flavor. The toasting step is commonly of 20-60 seconds duration.

Such methods are described in the following publications:

Rice: Chemistry and Technology ed D. F. Houston Amer. Assoc. Cereal Chemists, St. Paul, Minn, 1972 (see p402). The Chemistry & Technology of Cereals as Food & Feed ed S. A. Matz AVI Publishing Co. Inc. Westport Conn. 1959 (see p561).

Rice processed according to the present invention can be expanded and toasted to produce crisped rice having improved characteristics. The process is much more economical than has been possible by known methods.

Rice treated according to the invention results in greater expansion during toasting, lower bulk density and therefore lower caloric intensity per unit of bulk than existing forms of crisped rice commercially available. The surface of the expanded rice grains is smoother and is less damaged in handling. Importantly, by simple variation of the processing parameters, it is possible to vary the bulk density of the product as may be required for certain use applications for crisped rice, notably in the confectionery and snack-bar industry as well as in special bakery applications. It is also an important feature that the present invention is adaptable to the continuous production of crisped cereals, in contrast to the present batch-type operations used.

These steps are now described in the following example:

EXAMPLE 2

Parboiled medium grain Calrose rice was treated as follows.

Treatment A. 1 kg of rice at 12% moisture was mixed with sufficient water to increase the moisture content to 23% when fully absorbed. The complete absorption of the moisture by the rice required about 5 minutes. The dampened rice was held in a moisture-proof container for 15 hours at ambient temperature to allow uniform moisture penetration throughout the individual grains. The rice at ambient temperature was passed between the smooth rolls of a roller mill, in which the rolls rotated at the same speed. The gap between the rolls was set to 0.16 mm. The grains emerged flattened to an ovoid, disc-like shape. They were then dried to 13%-14% moisture and held in a moisture-proof container awaiting toasting.

Treatment B. The rice was treated as in treatment A except that the water used to moisten the rice to 23% moisture content contained 1 gram of a commercial amylase preparation BAN 240L (manufactured by NOVO INDUSTRI, Denmark) at the rate of 1 kg of dry rice used. It was noticed that in this treatment the rice was more separate and had a lesser tendency to display cohesiveness than in treatment A, even though in treatment A the tendency to cohesiveness between grains was very slight and became less as the moisture moved uniformly throughout the individual grains. After cold rolling, the grain was impregnated with salt as described in treatment E and F, and dried back to a moisture content of 13%-14%.

Treatment C. The rice was treated as in treatment B except that 20 g salt (sodium chloride) was dissolved in the water along with the commercial amylase preparation. No salt was added after cold-rolling and the rice dried back to a moisture content of 13%-14%.

Treatment D. The rice was treated as in treatment B, except that the solution contained, in addition to the amylase, 0.3 g of a commercial protease "NEUTRASE" (manufactured by NOVO INDUSTRI, Denmark) and in addition 20 g of salt (sodium chloride). No salt was added after cold-rolling and the rice dried back to a moisture content of 13%-14%.

Treatment E involved steaming the rice for 5 minutes at 100° C. in dry live steam, rolling while very hot through rolls set at a gap of 0.16 mm then impregnating with amylase and protease solution then with salt solution, tempering and finally drying to 13%-14% moisture content.

Treatment F resembled treatment D as far as enzyme usage was concerned, except that after the rice had been "cold-rolled" it was impregnated by tumbling with 70 milliliters of saturated sodium chloride solution per kg of dry rice used. This solution was very rapidly and totally absorbed by the cold-rolled rice in a matter of 2 or 3 minutes. After allowing about 15 minutes for the salt solution to penetrate throughout the cold-rolled rice, the rice was dried back to 13%-14% moisture content.

The CONTROL treatment was unprocessed parboiled white Calrose rice at 13%-14% moisture content.

In all of the above treatments the treated rice batches at 13%-14% moisture content were held in moisture-proof containers awaiting toasting to produce the final expanded crisped rice. Material at this stage, prior to toasting is called "half material". Half material may be held more or less indefinitely without change in expansion potential except for a slight decrease in bulk density potential on expansion, after the first 2 or 3 days storage.

The above described batches were toasted by placing some of the half-material in a stream of rapidly moving air at a temperature of about 230° C. until the rice was fully expanded and toasted to a light brown color. The expanded rice was then quickly cooled to ambient temperature in moving air and its bulk density was measured. This was done by determining the weight of the quantity of crisped rice which would fill a container of known cubic capacity. Bulk density was then expressed in "grams per liter". The lower the weight the "lighter" or more bulky the toasted product. The bulk densities of the treatments above described are given below:

| TREATMENT | BULK DENSITY | COMMENTS |
|---|---|---|
| Control | 250 g/li | Very poor product. |
| A | 138 g/li | Reasonable product - vastly superior to control. |
| B | 81 g/li | Excellent, very light, tender product, uniform expansion. |
| C | 99 g/li | Very good product. |
| D | 80 g/li | Excellent product, warm colour, extremely tender. |
| E | 145 g/li | Moderate product only - uneven expansion, lacking desired tenderness. |
| F | 76 g/li | Excellent product, warm colour, extremely tender, extremely even expansion. |

It is clear from the above results that "cold-rolling" is a very useful operation, but, in combination with low moisture enzyme treatment, outstanding results are obtained. By contrast, hot rolling, even in association with low moisture enzyme treatment gives a poorer result in relation to crisped grain products. For comparison, we have measured the bulk density of commercially marketed crisped rice products and found these to range from about 110 to 160 g/li. Such products are characterized by comprising a high proportion of less than whole grains whereas the preferred treatments embodying the present invention are characterized by causing no or almost no breakage of the rice into smaller pieces and thus comprising almost 100% whole-grain highly expanded and very tender crisped rice.

It has also been observed that these preferred treatments, when served with milk and sugar, as is a common method of eating, retained their crispness for a considerable time and were still crispy at the end of a reasonable period as required to consume a bowl of such cereal product.

The particular enzymes used in the above treatments are not limiting. Various types of amylases have been evaluated and have been found to be reasonably suitable. For example, as an alternative to BAN 240L, we have used "TERMAMYL", a high temperature amylase; PULLULANASE, an amylase having a specificity for breakage of 1,6 glucoside linkages; commercially available mixed enzymes such as "CEREMIX", and even enzyme active malt extract. (The names in inverted commas are the trade names of enzymes prepared by NOVO INDUSTRI of Denmark). The disadvantage of malt extract is in its sticky nature, not in its enzyme activity which, however, is not as well standardized as commercial enzymes. Protease used alone is less effective and it is necessary to use an amylase along with a protease to get the best result. Similarly the concentration of enzyme preparation used may be varied and is not limited to the concentration used in the above Examples. With BAN 240L, for example, use of 10% of the amount used in treatment B of Example 3 resulted in an increase in bulk density of only 6 grams per liter over that of the cited example.

EXAMPLE 3

In Example 2 the preferred treatments involved holding the dampened rice at 23% moisture at ambient temperature for several hours or overnight to allow the moisture to spread uniformly throughout the individual grains. While this lengthy tempering at ambient temperature is preferred if it is desired to produce a product of very low bulk density, shorter tempering periods may be used at temperatures which are above ambient but below a temperature at which deretrogradation of the gelatinized starch may occur.

Parboiled medium grain rice (var. Calrose) was treated with a solution containing BAN 240L (0.1% relative to the weight of rice) to increase its moisture content to 23%. As soon as this free liquid was absorbed by the rice (about 5 minutes) three aliquots were transferred to a microwave oven and the temperature of the rice samples was increased to 50° C. These three aliquots were held at 50° C. for 20 mins, 35 mins and 50 mins (G, H, I) without loss of moisture then rolled immediately as in previous examples, between smooth rolls set at a gap of 0.16 mm. Salt solution was added as in treatment F, Example 2, and the samples were then dried to 13%-14% moisture. A fourth aliquot was held at ambient temperature overnight without loss of moisture, treated with salt solution and dried back to 13%-14% moisture (J). Treatments G, H, I and J were toasted as in Example 2 and the bulk densities measured. Results are as in the following table:

| TREATMENT | BULK DENSITY | COMMENTS |
|---|---|---|
| G | 101 g/li | Treatments G, H and I were all very |
| H | 104 g/li | Good products, very tender texture |
| I | 105 g/li | and even expansion. |
| J | 87 g/li | Excellent product. |

While treatment J was slightly superior in its lightness to treatments G, H & I, the three latter products were all of very fine quality and have been judged equal or superior to commercially available crisped rice. The very important point in this example is that the period of time during which rice is "in process" is as little as 30-40 mins—that is, allowing for production from the raw material to half material. Such a process could be carried out on a continuous basis using fairly simple commonly available cereal processing equipment.

While the above examples have described the processing of whole grain parboiled medium grain rice, the process may also be applied to broken parboiled rice. Such broken rice is often available at lower cost. Alternately, if for special applications small particles of crisped rice are required, whole grain parboiled rice may be cut transversely using special equipment well known and readily available to industries engaged in cereal processing. Certain minor adaptations may be required when processing broken or cut rice.

The moisture content at which cold-rolling is carried out need only be as high as is necessary to have the grains pass between the suitably adjusted rolls without shattering or cracking or being rendered unduly fragile for further handling, storage and expansion. The gap between the rolls and the preferred moisture content may vary from grain type to grain type and variety to variety, as well as being dependent on the nature of the particular roller mill being used. As has been previously stated, the preferred moisture content for cold-rolling is within the range 19%-26% though in some circumstances this range may be widened as stated to from 16% to 30% moisture. Experience with the described products will enable simple selection of suitable moisture content and roll gap adjustment for particular grades of raw materials and finished products.

EXAMPLE 4

Using dry parboiled white Calrose rice, the rice was treated with sufficient water to increase its moisture content to 23%, the water containing the amylase BAN 240L (manufactured by Novo Industri Denmark) at a rate of 1 g per kg of dry rice, as well as the protease NEUTRASE at a rate of 0.3 g per kg of dry rice. The rice was mixed with the solution of enzymes until the rice had completely absorbed the solution. This occurred in about 5 minutes, the rice was then transferred to a moisture-proof container and held for 16-18 hours at ambient temperature within the range of 20° C.-23° C. The rice was then divided into lots and further processed as follows in Treatments A and B.

Treatment A, the rice was cold-rolled with a gap between the rollers of 0.16 mm, then mixed with a saturated solution of sodium chloride at a rate of 70 ml per kg of dry rice. This solution was rapidly absorbed within a few minutes. After allowing a tempering period of 10 minutes, the rice was dried to about 13.5% moisture.

Treatment B, the rice was steamed for 5 minutes in live dry steam then hot-rolled immediately the rice was removed from the steamer between rolls set at a gap of 0.16 mm. Saturated sodium chloride was added at the same rate as in Treatment A, tempered and dried as in Treatment A.

Treatment C involved slightly dampening dry parboiled Calrose white rice with about 5% moisture followed by steaming for 5 minutes. Thereafter the rice was immediately hot rolled at a gap of 0.16 mm between the rollers. The rice was then mixed with saturated salt solution, which was completely absorbed within about 5 minutes. The rice was tempered and dried as in Treatment A.

All treatments were held in moisture-proof packages for a few days then expanded as described in Example 3. The bulk densities were measured thereafter, and compared with the control.

| TREATMENT | BULK DENSITY | COMMENTS |
|---|---|---|
| Control | 250 g/li | Very poor product. |
| A | 83 g/li | Excellent, very light tender product, uniform expansion. |
| B | 144 g/li | Rice grains reasonably tender. |
| C | 166 g/li | Extremely separate and superior to control. |

These results show very clearly that the effect of low moisture enzyme treatment followed by steaming results in a poorer quality product. By contrast, cold rolling produced a higher quality product in terms of bulk density, appearance and eating quality. Nonetheless, there is some effect of the enzyme treatment even in conjunction with hot rolling as evidenced by the contrast between Treatments B & C.

EXAMPLE 5

In this example is described the application of low moisture enzyme treatment to grains other than rice to produce expanded oven crisped products. It is emphasized that oven crisped products are quite distinct from "puffed" or "gun-puffed" products, which terms describe the much expanded products which result when the grains under certain conditions of pressure, moisture and temperature expand very suddenly when the pressure is suddenly released, using gun-puffing equipment.

In experiments with oven crisping of grains other than rice it has been found that the best results are obtained by use of "waxy" forms of the grains. By "waxy" is meant the grains are comprised of a very low or zero proportion of amylose starch in the starch fraction of the grain and a conversely very high or total proportion of amylopectin starch. While a small amount of expansion results when most non-waxy grains are treated and then oven toasted, the results obtained with most such grains have not to date resulted in final oven-crisped products having usefully low bulk densities, tenderness, crisp texture and attractive appearance.

Very good results have been achieved using selected types of barley, sorghum (or milo), corn (maize) having this so called "waxy" character as well as with waxy rice. The use of waxy grains for production of oven or high temperature crisped products for use as ready-to-eat breakfast cereals snack foods, quick-cooking products and for other uses, either by standard methods or in conjunction with cold rolling and low moisture enzyme treatment as described is completely novel.

In each case, in the first instance it is necessary to treat the raw grain by the process of parboiling, which involves steeping the raw grain in water or impregnating the grain with water, subjecting the moistened grain to moist heat, preferably under steam pressure for an appropriate time then drying the grain slowly to 12%-14% moisture. The hulls or bran layers of the grains may be removed by methods well understood by persons skilled in the process of milling rice. Parboiling is well described in the literature. In our tests fully hydrated grains have typically been heated under 15 psi gauge pressure of live steam for 30 minutes, though in some cases as little as 5 minutes is sufficient.

In contrast to standard operating steps for parboiling of grain we have found it is surprisingly beneficial to incorporate salt (sodium chloride) into the grain at the steeping stage or along with moisture impregnated into the grain by total absorption methods. Salt has a useful effect on ultimate expansion of the grain by oven toasting as well as a desirable effect on flavor. Salt is typically incorporated in this way at 1%-2% on a dry weight basis. The grain is then pressure cooked as described above. Naturally other substances can be incorporated into the grain along with the salt solution.

It is also an unexpected and surprising observation that the amount of steaming under pressure required for pre-moistened waxy grains is substantially less than for regular or non-waxy grains, having in mind production of breakfast cereals. Thus, we have found that as little as 5-10 minutes of steaming in live steam at 15 psi will suffice to treat pre-dampened waxy grains, whereas much longer periods of time are required (eg. corn 1-2 hours at 18 psi; wheat 90 minutes at 20 psi, see "Chemistry and Technology of Cereals as Food and Feed" Matz, AVI Publishing p. 554, 556, (1959) eg. rice-18-19-psi for 1 hour 50 minutes, 15 psi for 5 hours, see "Elements of Food Technology" eg N W Desrosier, (1977) AVI Publishing Co p. 167).

The advantage of this time saving is very important in the following respects:

1) Substantial energy saving
2) Substantially increased capacity of equipment
3) The pressure steaming process can be converted to a continuous basis, in place of the present batch basis, necessitated by cook times of 1-2 hours.

Parboiled and optionally polished barley of a suitable type was moistened to 24% moisture content along with an amylase and a protease in a manner described in examples for rice. After tempering for several hours or overnight, the treated barley was cold-rolled between rolls set at a gap of 0.16 mm, salt solution was then added and was totally and rapidly absorbed. The grain was dried to about 13.5% moisture at which moisture content it was stored.

Parboiled and optionally polished sorghum grain of a suitable type was moistened to 25% moisture content, the amount of moisture required containing an amylase and a protease as described for rice, along with salt (sodium chloride) at a rate of 2% relative to the weight of dry parboiled sorghum grain used. The grain, after it had absorbed the total quantity of water and its contained solutes, was held overnight without loss of moisture, then cold-rolled between rolls set at a gap of 0.08 mm. It was then dried to 13% moisture content and stored at this moisture content.

Dry corn grains of a suitable type were suitably hydrated, pressure cooked and dried, as has already been described, so as to produce a form of parboiled corn. By suitable milling procedures samples of vitreous parboiled grits were produced to two or three size categories in a manner similar to the dry milling of corn. Alternatively dry degerminated corn grits of a suitable type were hydrated, then pressure cooked to produce a form of parboiled corn grits. Using any one of the size grades of grits, moisture to 23% was added along with an amylase as previously described. All the added moisture along with the amylase was rapidly absorbed within a few minutes. The grain was held without moisture loss overnight, then cold rolled through rolls set at a gap of 0.24 mm a small amount of salt solution was then added and fully absorbed and the grits so treated were dried to 13.5% moisture, in which condition the treated grits were stored.

In the case of each grain treated and dried as above described, oven toasting was carried out in a manner described for rice in example 3. The following results were obtained:

| Grain Type | Bulk density after oven toasting |
|---|---|
| Barley | 129 g/li |
| Sorghum (milo) | 65 g/li |
| Maize grits | 110 g/li |

All the above products were very light, tender, crispy and of uniform attractive appearance. Results have indicated a similar response for these products to those observed and described for rice, with respect to effect of low moisture enzyme treatment, cold-rolling as compared to hot-rolling, and the synergistic effect of cold-rolling and low moisture enzyme treatment.

It is also within the scope of this invention to produce a flake by cold rolling of the grain as described, then to toast the flake directly without further significant drying. Such products are light, tender and of more expanded texture than normal flaked cereals.

The methods described herein for processing rice by means of cold-rolling or low moisture enzyme treatment, either separately or in combination, may also be applied to many other starch containing products such as cereals so as to achieve quick-cooking character and/or reduced cohesiveness or stickiness on cooking and also to achieve some novel crisped products displaying very light texture, low bulk density, extreme tenderness and pleasing flavor and mouthfeel. Some of the products which have been treated under controlled conditions as described to give a controlled degree of expansion may be used in certain snack-meal preparations whereby rapid moisture absorption results simply from the addition of very hot or boiling water to the expanded product.

We claim:

1. A process for preparing an improved grain product consisting essentially of treating parboiled grains with water or an aqueous solution or suspension, wherein said solution or suspension is absorbed by the grain thereby raising the moisture content of said grain to a range of 16% to 30%; maintaining said treated grain at a temperature below the gelatinization temperature of said grain; subjecting said grain held below its gelatinization temperature to compression, said compression effective to produce compressed grains without significant cracking of said grains; and, thereafter drying said compressed grains to obtain a quick cooking grain product.

2. The process of claim 1, wherein said parboiled grain is compressed by rolling.

3. The process of claim 1, wherein said grain is maintained at ambient temperature during compression.

4. The process of claim 1, wherein said grain is rice, barley, sorghum or corn.

5. The process of claim 1, wherein said grain is maintained at a temperature preventing de-retrogradation of gelatinized starch present in said grain.

6. The process of claim 1, which further comprises adding supplements selected from sodium chloride, sugars, flavorings, seasonings, preservatives, nutrients, anti-oxidants and mixtures thereof.

7. The process of claim 1, wherein said grain product has a re-scan de-retrogradation endotherm (RDE) less than or equal to the initial de-retrogradation endotherm (IDE) of said grain product as measured by a differential scanning calorimeter (DSC).

8. A process for preparing an improved grain product comprising treating parboiled grains with an aqueous solution or suspension wherein said solution or suspension is absorbed by the grain thereby raising the moisture content of said grain to a range of 16% to 30% moisture; subjecting said grain to compression, said compression effective to produce compressed grains without significant cracking of said grains and wherein the temperature of the grain is maintained below the gelatinization temperature of said grain prior to and during said compression; drying said compressed grain; and thereafter toasting said dried grain to obtain a crisped grain product.

9. The process of claim 8, which further comprises drying back said compressed grain to a moisture content between about 12% and 14% moisture.

10. The process of one of claims 1 or 8 wherein said aqueous solution or suspension contains at least one enzyme selected from amylases, proteases or mixtures thereof.

11. The process of claim 10 wherein said total absorption is complete within 3 to 20 minutes.

12. The process of claim 10 which further comprises drying back said compressed grain to a moisture content between about 12% and 14% moisture.

13. The process of claim 12 wherein said dried grain is toasted to produce a crisped grain product.

14. The product of the process of claim 13 wherein the bulk density of said product is less than about 110 g/li.

* * * * *